United States Patent [19]

Mach et al.

[11] Patent Number: 5,723,308
[45] Date of Patent: Mar. 3, 1998

[54] CULTURE MEDIUM FOR RAPID COUNT OF COLIFORM BACTERIA

[75] Inventors: Patrick A. Mach, Shorewood; Karen E. Hesselroth, South St. Paul; Carl A. Adams, Apple Valley; Debra L. Schwab, Stillwater, all of Minn.

[73] Assignee: Minnesota Mining and Manufacturing Company, St. Paul, Minn.

[21] Appl. No.: 613,549

[22] Filed: Mar. 11, 1996

Related U.S. Application Data

[63] Continuation of Ser. No. 292,494, Aug. 18, 1994, abandoned, which is a continuation-in-part of Ser. No. 62,311, May 14, 1993, Pat. No. 5,364,766.

[51] Int. Cl.$^6$ .............................. C12Q 1/04; C12N 1/00; G01N 21/00
[52] U.S. Cl. .............................. 435/34; 435/4; 435/29; 435/38; 435/39; 435/240.3; 435/240.31; 435/243; 435/252.33; 435/261; 435/299; 435/810; 435/849; 422/55; 422/56; 422/57; 422/61
[58] Field of Search .................. 435/34, 4, 29, 435/38, 39, 240.3, 240.31, 243, 252.33, 261, 299, 810, 849; 422/55, 56, 57, 61

[56] References Cited

U.S. PATENT DOCUMENTS

| | | | |
|---|---|---|---|
| 3,960,658 | 6/1976 | Avakian et al. | 435/34 |
| 4,335,205 | 6/1982 | Greenwood | 435/34 |
| 4,416,984 | 11/1983 | Wheeler, Jr. | 435/31 |
| 4,565,783 | 1/1986 | Hansen et al. | 435/299 |
| 4,775,621 | 10/1988 | Berkhoff et al. | 435/38 |
| 4,906,565 | 3/1990 | Vossen | 435/15 |
| 5,073,488 | 12/1991 | Matner et al. | 435/31 |
| 5,089,413 | 2/1992 | Nelson et al. | 435/254 |
| 5,232,838 | 8/1993 | Nelson et al. | 435/30 |
| 5,364,766 | 11/1994 | Mach et al. | 435/34 |

FOREIGN PATENT DOCUMENTS

| | | |
|---|---|---|
| 0 161 481 | 4/1988 | European Pat. Off. . |
| 2 059 435 | 4/1981 | United Kingdom . |
| WO 82/02563 | 8/1982 | WIPO . |

OTHER PUBLICATIONS

Barth, Chemical Abstract, vol. 99, p. 341, Ref. #118862e, 1983.

The Merck Index, Tenth Edition, p. 930 and pp. 1044–1045, 1983.

LeChevallier et al., "New Medium for Improved Recovery of Coliform Bacteria from Drinking Water", *Applied and Environmental Microbiology*, vol. 45, No. 2, pp. 484–492, Feb. 1983.

Abstract, Derwent Publications Ltd., AN 92–380047 & SU A 1,703,695, Jan. 7, 1992.

Pettibone, *Letters in Applied Microbiology*, vol. 15, pp. 190–192, 1992.

Gerasimenko et al., *Chemical Abstracts*, vol. 77, p. 398, Ref. #18158g, 1972.

BBL Manual of Products and Laboratory Procedures, Fifth Edition, 1973, pp. 131–132.

Moats et al., "Observations on Brilliant Green Agar with an H$_2$S Indicator", *Applied and Environmental Microbiology*, vol. 31, No. 3, pp.380–384, Mar. 1976.

Lin, "Membrane Filter Method for Recovery of Fecal Coliforms in Chlorinated Sewage Effluents", *Applied and Environmental Microbiology*, vol. 32, No. 4, pp. 547–552, Oct. 1976.

Costilow, "Biophysical Factors in Growth", Manual for Methods for General Bacteriology, Chapter 6, 1981.

Difco Manual, Dehydrated Cultured Media and Reagents for Microbiology, Tenth Edition, pp. 172–173 (1985).

*Applied and Environmental Microbiology*, 38:229–236 (1979).

Martains et al, *Biological Abstracts*, vol. 92, No. 12, Ref. #141153, 1991 (Water Res 25(10): 1279–1284, 1991).

Standridge et al, *Applied and Environmental Microbiology*, vol. 44, No. 4, pp. 1001–1003, Oct. 1982.

*Primary Examiner*—Cecilia J. Tsang
*Assistant Examiner*—Abdel A. Mohamed

[57] ABSTRACT

This invention generally relates to products and processes used to determine the presence of bacteria in a sample and particularly relates to a culture medium which may be used in products and processes to allow early detection and count of Enterobacteriaceae. The bacterial culture medium which facilitates the early detection and count of bacteria is a mixture of gelatin peptone and yeast extract, lactose or glucose, sodium chloride, bile salts, guar gum and an excess amount of a sulfonphthalein dye sufficient to provide a high concentration of dye in close proximity to the growing bacteria in order to allow detection and count of the growing bacteria.

26 Claims, 1 Drawing Sheet

CULTURE MEDIUM FOR RAPID COUNT OF COLIFORM BACTERIA

This is a continuation of Application Ser. No. 08/292,494 filed Aug. 18, 1994, now abandoned, which is a continuation-in-part of U.S. Ser. No. 08/062,311 filed May 14, 1993, U.S. Pat. No. 5,364,766.

This invention generally relates to products and processes used to determine the presence of bacteria in a sample and particularly relates to a culture medium which may be used in products and processes to allow a rapid count of Enterobacteriaceae including coliform bacteria.

BACKGROUND

Classical methods for determining the presence and number of bacteria in a sample are time consuming, tedious and labor intensive. Typically, a technician must prepare reagents and nutrients, mix the nutrients with agar, heat the mixture, pour the mixture into a petri dish, allow the agar to gel, obtain a test sample, dilute the test sample, add an aliquot of the diluted sample to the agar, incubate the inoculated plate for 24–48 hours and finally count the number of growing bacterial colonies in the petri dish. Products and processes which reduce the preparation time and which allow an earlier, rapid count of the bacteria would clearly be welcomed by those working in this field.

One example of a product which greatly simplifies the above preparation time is a dry culture device for growing microorganisms that is described in U.S. Pat. No. 4,565,783 to Hansen et al. In a typical device reported by Hansen et al., a cold-water soluble dry powder containing a gelling agent and microbial growth nutrients is coated on a waterproof substrate. A transparent, read-through cover sheet coated on a surface with an acrylate adhesive containing an indicating dye and powdered gelling agent are attached to the coated substrate.

When the device is used, a predetermined amount of an aqueous sample is typically placed in contact with the coated substrate and the cover sheet is placed over the sample and substrate. The aqueous sample hydrates the soluble dry powder which then forms a gelled medium capable of sustaining microbial growth. During the growth period, the indicator dye adhered to the cover sheet reacts in the presence of viable microorganisms to give a detectable response that allows visualization of bacterial colonies which are grown on the culture device. A dry culture device based on the report of Hansen et al. is commercially available as PETRIFILM™ Coliform Count plates (Catalog No. 6400, 3M, St. Paul, Minn.).

The dry culture devices of Hansen et al. are much simpler to use than conventional gelled agar medium/petri dish systems because there is no need for the user to heat and mix the growth medium, agar and other reagents and then add the mixture to petri dishes or pour plates. In addition, the devices of Hansen et al. are compact and easily disposed of and therefore are easier and safer to use.

In spite of the many advantages that the Hansen et al. devices have over conventional types of culture systems, the inoculated thin film plates must still be incubated for 24–48 hours before the number of bacteria may be determined. The ability to detect the presence or determine the number of bacteria at an earlier time may be very valuable in many circumstances. For example, earlier detection and rapid count of bacteria is important in the food industry. At the present time, the determination of bacteria only after an incubation time of 24–48 hours requires processors to delay distribution of food products and may allow the production of large amounts of contaminated products. Earlier detection of bacteria in food products would allow the processor to release food products for distribution at an earlier time period because contamination or lack of contamination could be established earlier. In addition, a processor would be able to locate and correct a source of bacterial contamination without having to discard large amounts of contaminated products. Thus, detection of bacterial contamination in less than 24–48 hours would be extremely beneficial to food product producers.

Although the food industry would clearly benefit by determining bacterial contamination at an earlier time, other industries would also welcome the opportunity to detect bacteria more quickly. A need exists for products and processes which allow the early detection and rapid count of enterobacteriaceae such as coliform bacteria.

SUMMARY OF THE INVENTION

This invention overcomes the deficiencies of current products and processes referred to above by providing products and processes which allow the early detection and rapid count of enterobacteriaceae such as coliform bacteria. One embodiment of the present invention is a bacterial culture medium which facilitates the early detection and rapid count of coliform bacteria growing in the medium. The medium is a mixture of tryptose, lactose, sodium chloride, bile salts, guar gum and an excess amount of phenol red sufficient to provide a high concentration of phenol red in close proximity to the growing bacteria in order to allow detection and count of the growing bacteria in less than 12 hours.

Alternatively a more broadly useful medium for Enterobacteriaceae replaces lactose with glucose in the medium. The preferred range of glucose content is 2.5–20 g/l.

A preferred liquid culture medium for coliform detection contains between about 7–14 g/l gelatin peptone and 3–18 g/l yeast extract or 10–20 g/l tryptose, 2.5–20 g/l lactose, 2.5–7.5 g/l sodium chloride, 1.35–1.65 g/l bile salts, 2.5–7.5 g/l guar gum and 0.16–5.0 g/l phenol red. A particularly preferred liquid culture medium contains about 15 g/l tryptose or 7 g/l gelatin peptone and 9 g/l yeast extract, 10 g/l lactose, 5 g/l sodium chloride, 1.5 g/l bile salts, 5 g/l guar gum and 1.25 g/l phenol red.

In a further variation of the medium other sulfonphthalein type indicators e.g. bromocresol purple and chlorophenol red have also been found to be useful at high concentrations to provide early detection of Enterobacteriaceae such as coliforms.

The culture medium of this invention may be used in broths, in agar or in thin film devices such as PETRIFILM plates. When used in PETRIFILM plates the culture medium is coated onto a surface of the device and the medium is preferably then dried. When the preferred culture medium is in a dry state on a thin film, the medium contains about 4.8 mg/in$^2$ tryptose, 1.6 mg/in$^2$ lactose, 1.6 mg/in$^2$ sodium chloride, 0.5 mg/in$^2$ bile salts, 1.6 mg/in$^2$ guar gum and 0.4 mg/in$^2$ phenol red. When the dried medium is rehydrated the above listed components of the culture media are in the same concentrations that are in the preferred liquid culture media. The dried medium can be partially or completely rehydrated before inoculation with test bacteria.

Another embodiment of this invention is a method for detecting the presence of Enterobacteriaceae such as coliform bacteria in a sample. To practice this method, an aliquot of the sample containing bacteria is added to a culture medium comprising tryptose, lactose or glucose, sodium chloride, bile salts, and an excess amount of sulfonphthalein indicator such as bromocresol purple, chlorophenol red or preferably phenol red sufficient to provide a high concentration of indicator in close proximity to the bacteria. The bacteria are then grown in the presence of the culture medium and the presence of bacteria is determined by detecting the color change of the indicator as the growing bacteria produce metabolites. Using this method, the detection and count of coliform bacteria is possible in less than about 12 hours and preferably in less than about 8 hours.

Detection of the bacteria such as coliform bacteria in the culture medium may be done visually or done using an instrument. A suitable instrument is described in the related U.S. patent application Ser. No. 08/168,681 filed Dec. 13, 1993, now abandoned.

Still another embodiment of this invention is a device to detect bacterial growth in a sample. A preferred device includes a self-supporting, waterproof substrate and a transparent cover sheet. The present culture medium is coated on the self-supporting, waterproof substrate and then dried in order to provide a high concentration of sulfonphthalein indicator such as phenol red in close proximity to growing bacteria in order to allow detection and count of the growing bacteria in less than 12 hours. Detection of bacteria growing on the device is readily made (either visually or using an instrument) when the purple or red color of the media changes to a yellow color in the presence of acidic bacterial metabolites typical of Enterobacteriaceae such as coliform bacteria.

In another alternative embodiment, the present culture medium also contains a second indicator, triphenyltetrazolium chloride. When used in the culture medium, this second indicator provides a confirmation of the early detection and rapid count of bacteria. More specifically, after the presence of coliform bacteria are detected by the color change of a sulfonphthalein indicator, the growing bacteria continue to produce acids. When enough growing, acid-producing colonies are present, the medium eventually completely changes color from red or purple to yellow. After about 24 hours and when the medium has changed from red or purple to yellow, it is possible to detect the color change of the triphenyltetrazolium chloride in the medium caused by growing colonies of bacteria. In the presence of bacteria, triphenyltetrazolium chloride changes to a red color. The color change of the triphenyltetrazolium chloride allows confirmation of the earlier counts associated with the color change of a sulfonphthalein indicator such as phenol red. This later confirmation is also aided by the presence of gas bubbles produced by the bacteria around the bacteria.

When triphenyltetrazolium chloride is used in the culture medium, preferred amounts of this indicator in the culture media are between about 0.025–0.250 g/L, a more preferred amount is about 0.150 g/L. When triphenyltetrazolium chloride is used on a thin film device, the dried medium preferably contains about 0.02 mg/in$^2$ (0.0031 mg/cm$^2$) triphenyltetrazolium chloride. The triphenyltetrazolium chloride may be provided as part of culture medium 14 or may be a part of a coating on the cover sheet.

DETAILED DESCRIPTION

Figure 1:
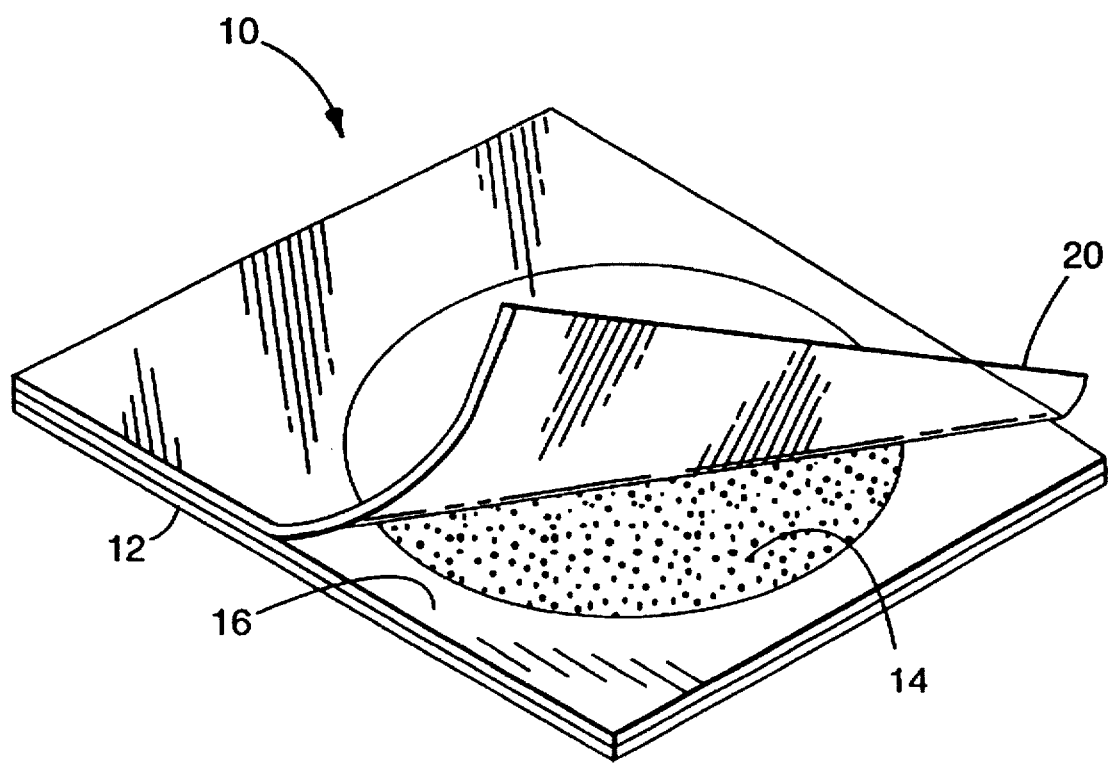
FIG. 1 is an illustration of a device containing the culture medium of the present invention.

This invention provides products and processes which may be used to detect the presence of Enterobacteriaceae, including coliform bacteria, in a sample in less than about 12 hours (coliform bacteria include lactose fermenting, gram-negative rods while other Enterobacteriaceae may utilize glucose). Although a variety of products and processes have been used to detect Enterobacteriaceae, particularly coliform bacteria, a detection and count time of less than 12 hours is significantly shorter than the detection times of conventional products or processes.

Early detection and rapid count of coliform bacteria in most samples has been problematic for a variety of reasons. In most cases, coliform bacteria present in samples have been stressed and are not growing at an optimal level. In order to provide for optimal growth (and thus allow early detection) the stressed bacteria must be provided a period of time to recover from induced stress. The present invention provides a medium which is believed to afford rapid recovery of coliform bacteria. This medium includes known reagents and nutrients which are commercially available. These reagents and nutrients include a mixture of peptone and yeast extract such as tryptose, lactose, sodium chloride, and bile salts which are available from Accumedia, Inc., Baltimore, Md. The medium also contains guar gum which is commercially available from Rhone-Poulenc, Inc., Kreuzlinger, Switzerland, phenol red which is commercially available from Aldrich Chemical Corp., Milwaukee, Wis., and triphenyltetrazolium chloride which is commercially available from AMRESCO, Solon, Ohio. The preferred reagents and materials are weighed and mixed using conventional procedures.

The present culture medium includes a sulfonphthalein pH indicator, for example phenol red, bromocresol purple, chlorophenol red and the like. These indicators provide similar results, with variations due to the pH at which color changes occur. Bromocresol purple changes from purple at and above pH 6.8 to yellow at and below pH 5.2. Phenol red is red at pH 8.2 and changes to yellow at pH 6.8. Chlorophenol red is red at pH 6.2 and changes to yellow at pH 4.8. These variations allow tailoring of the indicator system when a medium which changes at a slightly different pH is desired. The phenolsulfonphthalein nucleus upon which these dyes are based is shown below.

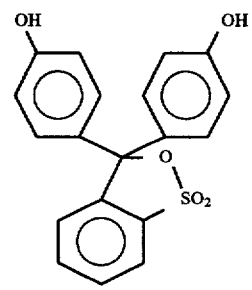

Because these indicators have a common nucleus, they share similar desirable properties such as adequate water solubility and relatively low toxicity to Enterobacteriaceae.

In particular, the present culture medium includes the preferred pH indicator phenol red. Phenol red is a known indicator which changes color from red to yellow in the presence of acid. As a bacterial colony grows, the colony produces metabolic acids which react with the indicator and produce yellow colored areas surrounding the colony. This indicator has been used in other culture media but is generally used in very small amounts, typically less than about 10–30 mg/l (Manual of Methods of General Bacteriology, page 440 (1981)). Specifically, phenol red has been reported in several culture media at levels of between about 18–24 mg/l (BBL Manual of Products and Laboratory Procedures, page 131 (1973)). According to the present invention, however, the amounts of phenol red are substantially greater than the amounts of phenol red, or other indicators, that are generally used in reported culture media. For example, use of about a ten-fold excess of phenol red over amounts used in conventional media, more than 160 mg of phenol red per liter, provides early detection and rapid count benefits. Furthermore, use of about a thousand-fold excess over amounts used in conventional media, more than 1000 mg of phenol red per liter, provides enhanced color contrast and is the preferred concentration in the present medium.

Surprisingly, coliform bacteria appear to recover and grow extremely well in medium which contains such a large excess of a sulfonphthalein indicator such as phenol red and there is apparently no toxicity to the coliform bacteria at these concentrations. As much as about 5000 mg of phenol red per liter, the upper limit of solubility for phenol red in water, has been found to be non-toxic to coliform bacteria. It may be that the large excess of phenol red serves to act as a buffer for the medium and therefore promotes recovery and/or growth because it is believed that coliform bacterial growth may be sensitive to pH. The use of amounts of phenol red which are sufficient to provide buffering capacity to the medium is not accepted practice because indicators are generally not reagents that are either used in large amounts or are selected to provide buffering capacity to a solution.

Another benefit of the ability to use excess amounts of sulfonphthalein indicators such as phenol red in the medium in order to provide some buffering capability to the medium is the prevention of diffusion of metabolic acids in the medium. Uncontrolled diffusion of acids through the medium may allow the yellow colored areas which surround growing colonies to overlap or run together. When the yellow colored areas overlap or run together, the resulting colony counts are either difficult to obtain or inaccurate.

Another unexpected benefit of using a large excess of bromocresol purple, phenol red or chlorophenol red is that the contrast between the strong e.g., bright red color of phenol red or bright red-violet of chlorophenol red or purple of bromocresol purple in neutral or basic solutions and the yellow color of bromocresol purple, phenol red or chlorophenol red in the presence of acid is maximized. The maximum contrast between the bright color of the medium and yellow color of the zones surrounding growing coliform bacteria allows visual detection of coliform bacteria at a much earlier time compared to the detection time of conventional products or processes.

In this specification, the phrase "excess mount of phenol red sufficient to cause a high concentration of phenol red in close proximity to the growing bacteria in order to allow detection and count of the growing bacteria in less than 12 hours" means a concentration of phenol red or an equivalent sulfonphthalein indicator greater than about 160 mg/l which allows for the visualization or instrument detection of a color change from purple or red to yellow caused by coliform bacterial metabolites.

In another variation the indicator medium includes a buffer, preferably a buffer which provides an optimum at about pH 7 such as a phosphate buffer comprising monobasic and dibasic sodium phosphate. This variation is particularly useful when it is desired to limit the size of the dye zones to smaller areas.

FIG. 1 illustrates a thin film culture device suitable for use with the media of the present invention. Briefly, the device is described in U.S. Pat. No. 4,565,783 and U.S. Pat. No. 5,089,413 which are incorporated by reference in this application for the purposes of describing the processes of making and using these types of culture devices.

The thin film culture device 10 includes a body member having a self-supporting, waterproof substrate 12. Substrate 12 is preferably a relatively stiff material made of a waterproof material that does not absorb water such as polyester, polypropylene, or polystyrene. Other suitable waterproof materials include substrates such as paper containing a waterproof polyethylene coating.

The upper surface of substrate 12 is coated with a layer of culture medium 14 which is then dried to provide a dry medium on substrate 12. Alternatively, a layer of adhesive may be coated on substrate 12, which adhesive serves to hold a culture medium which may be applied as a powder. The adhesive should be sufficiently transparent when hydrated to allow viewing of bacterial colonies growing on the surface of the substrate through the coated substrate. The adhesive should also be coated on the substrate in a thickness which allows the substrate to be uniformly coated with dry culture medium without completely embedding the media in the adhesive.

If the liquid culture medium of this invention is to be used in a dry form or as a dry powder, the reagents, nutrients and indicator such as phenol red are dried. The culture medium of this invention may be readily dried by heating liquid medium in an oven about at 220° F. until essentially all of the water in the liquid has evaporated. If the medium is heated after the water has evaporated, however, the medium begins to degrade.

A foam spacer 16 having a circular opening in the foam is adhered to the medium coated surface of substrate 12. The foam spacer which covers the periphery of substrate 12 defines the area which is to be inoculated with a sample and serves to prevent the sample from leaking from the substrate. In an alternate embodiment, a device may not include a sample-containing foam layer. In this device, the amount of sample is contained on the substrate by the components of the medium alone.

A cover sheet 20 is attached to one edge of an upper surface of the foam spacer 16. Cover sheet 20 is preferably made of a transparent film or sheet material in order to facilitate counting of bacterial colonies present on the substrate. In addition, cover sheet 20 is preferably impermeable to bacteria and water vapor in order to avoid the risk of contamination and deterioration of the components. A preferred material for use as a cover sheet 20 is biaxially-oriented polypropylene.

In use, a predetermined amount of inoculum, typically about one milliliter of inoculum, is added to the device illustrated in FIG. 1 by pulling back cover sheet 20 and adding an aqueous test sample or water to the middle of substrate 12. Cover sheet 20 is then replaced over substrate 12 and the inoculum is evenly spread on the substrate. A convenient tool to do this is a weighted circular template which also is used to confine the inoculum to a specific area of substrate 12. As the inoculum contacts and is spread on substrate 12, the culture medium on substrate 12 hydrates to form a growth-supporting nutrient gel. The inoculated device is then incubated for a predetermined time after which the number of bacterial colonies growing on the substrate may be counted through the transparent cover sheet 20.

Although the use of the culture medium of this invention on a thin film device is described above, those of ordinary skill in the art will recognize that the culture media may be used in other culturing devices which are known in the art. For example, the culture medium may be used as a broth and used to grow bacteria in suspension or the culture media may be use to grow bacteria on known agar plates.

The following examples are intended to provide further details and embodiments related to the practice of the present invention. These examples are provided for illustrative purposes and should not be construed to limit the scope of the present invention which is defined in the appended claims.

EXAMPLE 1

Growth of Coliform Bacteria in Rapid Coliform Count Medium

This example illustrates that a preferred liquid medium of this invention (rapid coliform count medium, RCCM) may be used to grow coliform bacteria in a broth, in agar, or in a thin film plate. The medium used in this example contained 15 g/l tryptose, 5 g/l lactose, 5 g/l sodium chloride, 1.5 g/l bile salts, 5 g/l guar gum, 0.050 g/l triphenyltetrazolium chloride and 1.25 g/l phenol red (all components were commercially available from the sources listed above) which the exception that no triphenyltetrazolium chloride was used in the broth medium.

Various bacteria listed in Table 1, below, were initially grown for 18–24 hours in trypticase soy broth (Difco Laboratories, Inc., Detroit, Mich. at 35° C. The bacteria listed in Table 1 were either purchased from Sillicker Laboratories, Chicago, Ill. (indicated by "s" after bacteria name) or were quality control isolates used by 3M Microbiology Products Laboratory, St. Paul, Minn. Those of ordinary skill will recognize that equivalent strains or species of bacteria are commercially available or may be isolated using well known methods or processes.

After about 24 hours of growth in the trypticase soy broth, the growing cultures containing about $10^8$–$10^9$ bacteria/ml were serially diluted about $10^6$–$10^7$ fold in Butterfields Standard Methods Buffer (SMB, Fisher Scientific, Minneapolis, Minn.). An aliquot of the diluted culture (about one ml) was used to inoculate a petri dish, a screw-cap glass tube or a PETRIFILM plate containing RCCM.

For growth in agar, the culture aliquots were added to petri dishes and were then overlaid with RCCM and agar (about 12 ml of medium containing about one wt./vol. % agar) and then incubated for 24 hours at 35° C. For growth in a broth, the culture aliquots were added to the screw-cap tubes containing RCCM (about 10 ml) and a durham tube. The tubes were then capped and also incubated for 24 hours at 35° C.

For growth on a thin film, a layer of RCCM was forced through a small orifice in order to cover a 7.5 mil polyester substrate film (Imperial Chemical Industries, Wilmington, Del.) at room temperature. The covered polyester film was then dried for between about 1–20 minutes at about 200°–250° F. An 18 mil styrofoam spacer sheet was cut to cover the polyester film and a circular opening was cut in the styrofoam spacer. One surface of the cut styrofoam spacer was coated with an isooctyl acrylate/acrylamide pressure sensitive adhesive (96/4 wt. % ratio of acrylate to acrylamide) and the styrofoam sheet was adhered to the coated surface of the polyester film.

A transparent polypropylene film was cut to cover the polyester/styrofoam laminated film. One surface of the polypropylene film (1.6 mil, 3M, St. Paul, Minn.) was coated with an isooctyl acrylate/acrylamide pressure sensitive adhesive (96/4 wt. % ratio of acrylate to acrylamide) and coated with a layer of guar gum (Rhone-Poulenc, Inc. Kreuzlinger, Switzerland). A layer of double-sided adhesive coated tape (3M, St. Paul, Minn.) was placed on one exposed edge of the styrofoam spacer and the gum-containing surface of the polypropylene film was adhered to the styrofoam spacer along one edge.

The culture aliquots (one ml) were placed in the opening of the styrofoam spacer, the polypropylene film was used to cover the inoculum, and the thin film was incubated for 24 hours at 35° C.

After incubation for 24 hours, the petri dishes, glass tubes and thin film plates were evaluated for the presence of acid zones which were identified as yellow areas on the red background of the plate or dish and/or for the presence of gas bubbles. Broth cultures were evaluated for change in color from red to yellow and for the presence of gas bubbles in the durham tubes.

The data listed in Table 1 below indicate that RCCM was selective for growing coliform bacteria.

TABLE 1

| Bacteria | Inoculum (Cfu/TSA) | RCCM - broth Growth | Acid/Gas | RCCM - Agar Growth | Acid | RCCM - Thin Film Growth | Acid/Gas | PETRIFILM CC plate Growth | Acid/Gas |
|---|---|---|---|---|---|---|---|---|---|
| E. coli 565s | 30 | G | (+/+) | G | (+) | — | | — | |
| E. coli 471s | 66 | G | (+/+) | G | (+) | — | | — | |
| S. sap. 789s | 43 | NG | (−/−) | NG | (−) | NG | | NG | |
| B. pum 1212s | 10 | NG | (−/−) | NG | (−) | NG | | NG | |
| E. fecaelis EN1094 | 43 | NG | (−/−) | NG | (−) | NG | | NG | |
| S. aureus 50s | 41 | NG | (−/−) | NG | (−) | NG | | NG | |
| E. fecaelis SF | 39 | NG | (−/−) | NG | (−) | NG | | NG | |
| E. fecaelis 3M | 37 | NG | (−/−) | NG | (−) | NG | | NG | |
| S. aureus 48s | 117 | NG | (−/−) | NG | (−) | NG | | NG | |
| L. dulbreckii 914s | 40 | NG | (−/−) | NG | (−) | NG | (−/−) | NG | (−/−) |
| S. typhimurium 451s | 95 | G | (−/−) | G | (−) | G | (+/−) | G | (−/−) |
| Y. ent. 572s | 93 | G | (+/+) | G | (+) | G | | G | |
| L. monocytog 23s | 70 | NG | (−/−) | G | (−) | NG | | NG | |
| E. fecaelis 73s | 20 | NG | (−/−) | NG | (−) | NG | | NG | |
| S. saintpaul 373s | 49 | G | (−/−) | G | (−) | ND | (−/−) | ND | (−/−) |
| P. vulgaris 760s | 60 | G | (+/−) | G | (−) | G | | G | |

TABLE 1-continued

| Bacteria | Inoculum (Cfu/TSA) | RCCM - broth Growth | RCCM - broth Acid/Gas | RCCM - Agar Growth | RCCM - Agar Acid | RCCM - Thin Film Growth | RCCM - Thin Film Acid/Gas | PETRIFILM CC plate Growth | PETRIFILM CC plate Acid/Gas |
|---|---|---|---|---|---|---|---|---|---|
| E. coli 503s | 42 | G | (+/+) | G | (+) | ND | | ND | |
| C. freundii 614s | 29 | G | (+/+) | G | (+) | ND | | ND | |
| C. freundii 433s | 27 | G | (+/+) | G | (+) | ND | | ND | |
| E. coli 563s | 53 | G | (+/+) | G | (+) | ND | | ND | |
| K. pneu 26 | 49 | G | (+/+) | G | (+) | ND | | ND | |
| E. aerog 39 | 95 | G | (+/+) | G | (+) | ND | | ND | |
| E. agglomerans 44s | 41 | G | (+/+) | G | (+) | ND | | ND | |
| E. coli 555s | 94 | G | (+/+) | G | (+) | ND | (+/+) | ND | (+/+) |
| E. cloacae C5 | 98 | G | (+/+) | G | (+) | G | | G | |
| S. newport 347s | 92 | G | (+/-) | G | (+) | ND | (+/+) | ND | (+/+) |
| E. sakazaki C3 | 73 | G | (+/+) | G | (+) | G | (+/+) | G | (+/+) |
| K. oxytoca C4 | 48 | G | (+/+) | G | (+) | G | (+/+) | G | (+/+) |
| H. alvei C2 | 80 | G | (+/+) | G | (+) | G | (+/+) | G | (+/+) |
| S. liquefaciens C1 | 75 | G | (+/+) | G | (+) | G | | G | |
| E. coli 561s | 76 | G | (+/+) | G | (+) | ND | | ND | |
| C. freundii 17 | 96 | G | (+/+) | G | (+) | ND | | ND | |
| K. oxytoca 33 | 97 | G | (+/+) | G | (+) | ND | (+/+) | ND | (+/+) |
| E. coli 149 | 80 | G | (+/+) | NG | (−) | G | | G | |
| E. fecaelis EN1062 | 70 | NG | (−/−) | G | (+) | NG | | NG | |
| E. coli 627s | 86 | G | (+/+) | G | (+) | ND | | ND | |
| E. aggl 611s | 136 | G | (+/−) | G | (+) | ND | | ND | |
| E. coli 633s | 71 | G | (+/+) | NG | (−) | ND | | ND | |
| Blank | 0 | NG | (−/−) | NG | (−) | NG | | NG | |

G — growth
NG — no growth
ND — not determined
Gas — (−) no gas bubbles, (+) gas bubbles
Acid — (−) no acid zone, (+) acid zone

EXAMPLE 2

Concentration Effect of Indicator Dye

This example indicates that excess amounts of indicator dye such as phenol red, i.e. amounts of phenol red greater than about 160 mg/l provide early detection and count of coliform bacteria. In this example, various bacteria were quality control isolates used by 3M Microbiology Products Laboratory, St. Paul, Minn. These bacteria included *Serratia liquefaciens* (3M strain C1 which was used at three different dilutions; about 25 bacteria/ml, 50 bacteria/ml and 75 bacteria/ml), *Hafnia alvei* (3M strain C2), *Enterobacter sakazaki* (3M strain C3), *Klebsiella oxytoca* (3M strain C4), *Enterobacter cloacae* (3M strain C5), and *Escherichia coli* (*E. coli* 149, ATCC Accession Number 55535 which was used at three different dilutions; about 25 bacteria/ml, 50 bacteria/ml and 75 bacteria/ml). Equivalent strains or species of bacteria would be readily recognized by those of ordinary skill in the art. The bacteria were grown and diluted as described in Example 1 and culture aliquots were added to thin film plates as described in Example 1 with the exception that the concentrations of phenol red in the medium coated on the polyester film varied from 0.04–2.5 g/l.

The data in Table 2, below, list the percentage of colonies which were counted at 12 hours compared to the number of colonies which were counted at 24 hours. The 24 hour count was made by identifying colonies which produced gas and which were detected by the color change of triphenyltetrazolium chloride. The data indicate that amounts of phenol red in excesses of 160 mg/l allowed consistent early detection and rapid count as well as provided faster quantification of acid producing bacteria.

TABLE 2

Concentration Effect of Phenol Red

| phenol red g/l | C1 25 bac/ml | C1 50 bac/ml | C1 75 bac/ml | C2 | C3 | C4 | C5 | 149 25 bac/ml | 149 50 bac ml | 149 75 bac/ml |
|---|---|---|---|---|---|---|---|---|---|---|
| 2.50 | 96.30 | 110.0 | 95.56 | 97.16 | 97.50 | 97.92 | 105.8 | — | — | 88.55 9 hr |
| 1.25 | 97.06 | 103.5 | 95.83 | 94.07 | 106.0 | 97.22 | 57.59 | — | 107.8 10 hr | 97.27 9 hr |
| 0.63 | 118.8 | 107.7 | 102.6 | 98.79 | 102.2 | 95.28 | 100.0 | 101.2 | — | 106.8 9 hr |
| 0.31 | 103.7 | 126.1 | 95.00 | 83.54 | 93.18 | — | 100.0 | — | — | 94.74 9 hr |
| 0.16 | 97.22 | 107.4 | 88.70 | — | — | — | 100.0 | 100.0 | — | — |
| 0.08 | 103.6 | — | 93.06 | — | 96.00 | — | 100.0 | — | — | — |

TABLE 2-continued

Concentration Effect of Phenol Red

| | | | | | bacteria strains | | | | | |
|---|---|---|---|---|---|---|---|---|---|---|
| phenol red g/l | C1 25 bac/ml | C1 50 bac/ml | C1 75 bac/ml | C2 | C3 | C4 | C5 | 149 25 bac/ml | 149 50 bac ml | 149 75 bac/ml |
| 0.04 | 100.0 | — | 71.88 | — | 104.8 | — | 93.62 | — | — | — |

EXAMPLE 3

Comparative Example

In one experiment, thin film plates containing the culture media of this invention (RCCM) were compared to commercially available PETRIFILM coliform count plates (3M, St. Paul, Minn.) and to conventional pour plates containing Violet Red Bile Agar (Difco Laboratories, Inc.).

Thin film plates containing RCCM were prepared as described in Example 1.

Aliquots used to inoculate the thin film plates were taken from milk samples available on request from the Dairy Quality Control Institute, Minneapolis, Minn. which were diluted as described in Example 1. For each different sample, aliquots (one ml) were added to three plates each having a different type of media and then the inoculated plates were incubated at 35° C. Each of the inoculated plates were evaluated visually every hour.

In addition, both RCCM and the PETRIFILM thin film plates were evaluated every thirty minutes by imaging the plates with a camera at two different wavelengths. The images at both wavelengths were then digitized and stored electronically. The stored images were further processed by dividing the images of the two wavelengths and then subtracting the divided image from the divided image calculated from the images made thirty minutes earlier. This process of image analysis is described in related U.S. patent application Ser. No. 07/912,887 filed Jul. 13, 1992 which is incorporated by reference in this application for the purposes of recording and analyzing such images.

The detection and count of colony forming units from the three media were determined manually.

The data provided by the above described comparison are listed in Table 3 below. The data establish that the media of this invention allow earlier detection and count when compared to either of the other media.

TABLE 3

| MEDIA | COLONY-FORMING UNITS/ML (duplicate plates) | TIME (HOURS) |
|---|---|---|
| Violet Red Bile Agar | 41/31 | 24 |
| PETRIFILM coliform count plates | 15/15 | 24 |
| RCCM (visual) | 31/39 | 10 |
| RCCM (instrument) | 36/35 | 8 |

In another experiment, thin film plates containing the culture media of this invention were compared to commercially available PETRIFILM coliform count plates (3M, St. Paul, Minn.), to a modified PETRIFILM coliform count plate having either phenol red or neutral red (another commonly used indicator available from Sigma-Aldrich Corp., Milwaukee, Wis. and to a thin film plate coated with a medium which was identical to RCCM except that phenol red was replaced with neutral red, a different commonly used indicator.

Thin film plates containing the different media and indicators were prepared as described in Example 1 and were inoculated with aliquots of diluted sample containing the bacteria listed in Table 4, below. The bacteria used in this example were used in Example 2, above. The data indicate the time needed to count one hundred percent of the colonies which where observed after 24 hours as detected by the color change of triphenyltetrazolium chloride and the formation of gas bubbles.

TABLE 4

Time to Achieve Count Equivalent to 24 Hour Count

| | bacteria | | | | | |
|---|---|---|---|---|---|---|
| medium - indicator | C1 | C2 | C3 | C4 | C5 | 149 |
| RCCM phenol red | 9 hr | 11 hr | 12 hr | 9 hr | 12 hr | 10 hr |
| RCCM neutral red | CNR | CNR | CNR | CNR | CNR | CNR |
| PCC phenol red | 10 hr | 10 hr | 12 hr | 8 hr | 12 hr | 9 hr |
| PCC neutral red | CNR | CNR | 13 hr | CNR | CNR | CNR |

CNR — counts not readable
24 hr determined by the formation of gas bubbles and color change of triphenyltetrazolium chloride
PCC = Petrifilm Coliform Count plates (see also pf cc)

EXAMPLE 4

Comparative Example

In this experiment, thin film plates containing variations of the culture media of this invention (RCCM and RECM) were compared to commercially available PETRIFILM coliform count plates (pf cc) (3M, St. Paul, Minn.) which use neutral red as the indicator dye.

Thin film plates containing RCCM and RECM were prepared as described in Example 1. However, the amounts differ somewhat and monobasic and dibasic potassium phosphate are added as shown in Table 5 below.

TABLE 5

Media* Formulations

| Ingredient | Coliform (RCCM) | Enterobacteriaceae (RECM) |
|---|---|---|
| Peptone G[1] | 14 g/L | 14 g/L |
| Yeast Extract[1] | 18 g/L | 6 g/L |
| Sodium Chloride[2] | 10 g/L | 10 g/L |
| Bile salts[1] | 3 g/L | 3 g/L |
| Potassium Phosphate, Monobasic[3] | 2 g/L | 2 g/L |
| Potassium Phosphate, Dibasic[3] | 6 g/L | 6 g/L |
| Lactose[1] | 20 g/L | — |

TABLE 5-continued

| Ingredient | Media* Formulations | |
|---|---|---|
| | Coliform (RCCM) | Enterobacteriaceae (RECM) |
| Glucose[1] | — | 20 g/L |
| Guar Gum[4] | 10 g/L | 11 g/L |
| Deionized water, pH = 7.0 = /−0.1 | 1 liter | 1 liter |

Ingredient Sources
[1]Accumedia
[2]Sigma Chemical Company
[3]Mallinckrodt
[4]Rhone-Poulenc
*Coating solutions are two times the final coating weight.

To the media formulations were added one of the dyes bromocresol purple, chlorophenol red or phenol red (available from Accumedia) at coating concentrations (twice the final (dried) concentration) as shown in Table 5 and the formulations were knife coated onto the backing and dried at 220° F. (104° C.) for 5 to 10 minutes.

The bacterium $E.$ $coli$ 149 (ATCC No. 55535) was grown overnight at 35° C. in Tryptic soy broth (Dimed Corporation, St. Paul, Minn.). The culture was diluted approximately $10^{-7}$-fold in Butterfields Buffer (Fischer Scientific, Chicago, Ill.) to approximately 20–50 colony-forming units/milliliter. Duplicate plates of each dye type and concentration were inoculated with 1 milliliter of the bacterial suspension and incubated at 35° C. for the remainder of the experiment. Plates were viewed for the presence of yellow zones, indicating the presence of acid forming bacteria. The results are presented as a percentage of the final number of colonies at 24 hours on the plates in Table 6 and Table 7.

These results show that all of the sulfonphthalein dyes provide more rapid detection of Enterobacteriaceae when the dyes are used at high concentrations.

TABLE 6

E. coli counts in Enterobacteriaceae Medium (RECM)

| Time (h) | EB/NR (0.09) | BCP (1.25) | CPR (1.25) | PR (1.25) | BCP (0.03) | CPR (0.03) | PR (0.03) |
|---|---|---|---|---|---|---|---|
| MEAN RAW COUNTS | | | | | | | |
| 6 | 0.0 | 0.0 | 0.0 | 0.0 | 0.0 | 0.0 | 0.0 |
| 7 | 0.0 | 0.0 | 0.0 | 0.0 | 0.0 | 0.0 | 0.0 |
| 8 | 0.0 | 8.5 | 0.0 | 16.0 | 0.0 | 0.0 | 0.0 |
| 9 | 0.0 | 19.5 | 5.0 | 26.0 | 0.0 | 0.0 | 0.0 |
| 10 | 0.0 | 24.5 | 24.0 | 29.0 | 16.0 | 0.0 | 13.0 |
| 11 | 11.0 | 25.5 | 28.0 | 29.0 | 20.0 | 11.5 | 19.5 |
| 12 | 21.5 | 25.5 | 28.5 | 29.0 | 21.0 | 17.0 | 21.0 |
| 24 | 24.5 | 25.5 | 28.5 | 29.0 | 26.0 | 24.5 | 25.0 |
| PERCENT OF 24 h COUNTS | | | | | | | |
| 6 | 0.0 | 0.0 | 0.0 | 0.0 | 0.0 | 0.0 | 0.0 |
| 7 | 0.0 | 0.0 | 0.0 | 0.0 | 0.0 | 0.0 | 0.0 |
| 8 | 0.0 | 33.3 | 0.0 | 55.2 | 0.0 | 0.0 | 0.0 |
| 9 | 0.0 | 76.5 | 17.5 | 89.7 | 0.0 | 0.0 | 0.0 |
| 10 | 0.0 | 96.0 | 84.2 | 100.0 | 61.5 | 0.0 | 52.0 |
| 11 | 44.9 | 100.0 | 98.2 | 100.0 | 77.0 | 47.0 | 78.0 |
| 12 | 87.8 | 100.0 | 100.0 | 100.0 | 80.8 | 69.4 | 84.0 |
| 24 | 100.0 | 100.0 | 100.0 | 100.0 | 100.0 | 100.0 | 100.0 |

EB/NR = Enterobacteriaceae medium/neutral red indicator
BCP = bromcresol purple
CPR = chlorophenol red
PR = phenol red

TABLE 7

E. coli counts in Coliform Medium (RCCM)

| Time (h) | pf cc | BCP (1.25) | CPR (1.25) | PR (1.25) | BCP (0.03) | CPR (0.03) | PR (0.03) |
|---|---|---|---|---|---|---|---|
| MEAN RAW COUNTS | | | | | | | |
| 6 | 0.0 | 0.0 | 0.0 | 0.0 | 0.0 | 0.0 | 0.0 |
| 7 | 0.0 | 0.0 | 0.0 | 0.0 | 0.0 | 0.0 | 0.0 |
| 8 | 0.0 | 0.0 | 0.0 | 15.0 | 0.0 | 0.0 | 0.0 |
| 9 | 0.0 | 6.0 | 0.0 | 20.5 | 0.0 | 0.0 | 0.0 |
| 10 | 0.0 | 19.0 | 13.0 | 26.0 | 11.5 | 5.5 | 18.0 |
| 11 | 11.0 | 22.5 | 19.5 | 26.0 | 17.0 | 10.0 | 21.0 |
| 12 | 21.5 | 22.5 | 25.0 | 26.0 | 24.0 | 15.5 | 23.5 |
| 24 | 25.5 | 22.5 | 28.0 | 26.0 | 25.5 | 23.5 | 29.5 |
| PERCENT OF 24 h COUNTS | | | | | | | |
| 6 | 0.0 | 0.0 | 0.0 | 0.0 | 0.0 | 0.0 | 0.0 |
| 7 | 0.0 | 0.0 | 0.0 | 0.0 | 0.0 | 0.0 | 0.0 |
| 8 | 0.0 | 0.0 | 0.0 | 57.7 | 0.0 | 0.0 | 0.0 |
| 9 | 0.0 | 26.7 | 0.0 | 78.8 | 0.0 | 0.0 | 0.0 |
| 10 | 0.0 | 84.4 | 46.4 | 100.0 | 45.1 | 23.4 | 61.0 |
| 11 | 43.1 | 100.0 | 69.6 | 100.0 | 66.7 | 42.6 | 71.2 |
| 12 | 84.3 | 100.0 | 89.3 | 100.0 | 94.1 | 66.0 | 79.7 |
| 24 | 100.0 | 100.0 | 100.0 | 100.0 | 100.0 | 100.0 | 100.00 |

We claim:

1. A bacterial culture medium which facilitates the early detection and count of Enterobacteriaceae growing in the medium comprising tryptose or a mixture of gelatin peptone and yeast extract, lactose or glucose, sodium chloride, bile salts, guar gum and an excess amount of a sulfonphthalein dye sufficient to provide a high concentration of dye in close proximity to the growing bacteria in order to allow detection and count of the growing bacteria.

2. The culture medium of claim 1 wherein the concentration of the sulfonphthalein dye is in the range of about 160 mg/l to about 5000 mg/l.

3. The culture medium of claim 1 wherein the concentration of the sulfonphthalein dye is in the range of about 1000 mg/l to about 5000 mg/l.

4. The culture medium of claim 1 wherein the medium further comprises triphenyltetrazolium chloride.

5. The culture medium of claim 1 wherein the dye is selected from the group consisting of bromocresol purple, phenol red and chlorophenol red.

6. The culture medium of claim 5 containing about 10–20 g/l tryptose or 7–14 g/l gelatin peptone and 3–18 g/l yeast extract, 2.5–20 g/l lactose or 2.5–20 g/l glucose, 2.5–7.5 g/l sodium chloride, 1.35–1.65 g/l bile salts, 2.5–7.5 g/l guar gum, 0.025–0.250 g/l triphenyltetrazolium chloride, and 0.16–5.0 g/l dye.

7. The culture medium of claim 6 containing about 10–20 g/l tryptose or 7–14 g/l gelatin peptone and 3–18 g/l yeast extract, 2.5–20 g/l lactose or 2.5–20 g/l glucose, 2.5–7.5 g/l sodium chloride, 1.35–1.65 g/l bile salts, 2.5–7.5 g/l guar gum, 0.025–0.250 g/l triphenyltetrazolium chloride, and 1.0–5.0 g/l dye.

8. The culture medium of claim 1 containing about 15 g/l tryptose or 7 g/l gelatin peptone and 9 g/l yeast extract, 5 g/l lactose, 5 g/l sodium chloride, 1.5 g/l bile salts, 5 g/l guar gum, 0.150 g/l triphenyltetrazolium chloride and 1.25 g/l dye.

9. The culture medium of claim 8 further containing 2 g/l monobasic potassium phosphate and 6 g/l dibasic potassium phosphate.

10. The culture medium of claim 1 further comprising a buffer.

11. The culture medium of claim 10 wherein the buffer is a phosphate buffer.

12. A method of detecting the presence of Enterobacteriaceae in a sample comprising the steps of adding an aliquot of the sample containing bacteria to a culture medium comprising a mixture of gelatin peptone and yeast extract, lactose or glucose, sodium chloride, bile salts, guar gum and an excess amount of a dye sufficient to provide a high concentration of dye in close proximity to the bacteria; growing the bacteria in the presence of the culture medium; and detecting the color change of the dye as the growing bacteria metabolize.

13. The method of claim 12 wherein the bacteria are grown in agar containing the culture medium.

14. The method of claim 12 wherein the color change of the dye is detected visually.

15. The method of claim 12 wherein the color change of the dye is detected by an instrument.

16. The culture medium of claim 12 wherein the dye is selected from the group consisting bromocresol purple, phenol red and chlorophenol red.

17. The method of claim 12 wherein the culture medium further comprises a suitable buffer.

18. The method of claim 12 wherein the bacteria are grown in a suspension containing the medium.

19. The method of claim 18 wherein the bacteria are grown in a thin film containing the medium using a device having a self-supporting, waterproof substrate and a transparent cover sheet, wherein the culture media is coated on the waterproof substrate.

20. The method of claim 12 wherein the culture medium further comprises triphenyltetrazolium chloride.

21. The method of claim 20 further comprising the step confirming the presence of coliform bacteria in the sample by detecting gas formation and a color change in the triphenyltetrazolium chloride.

22. A device to detect coliform bacterial growth in a sample consisting essentially of a self-supporting, waterproof substrate, a foam spacer and a transparent cover sheet, wherein a culture medium comprising a mixture of gelatin peptone and yeast extract, lactose or glucose, sodium chloride, bile salts, guar gum and an excess amount of a sulfonphthalein dye is coated on the self-supporting, waterproof substrate sufficient to provide a high concentration of dye in close proximity of growing bacteria in order to allow detection and count of the growing bacteria.

23. The device of claim 22 wherein the dye changes color from red or purple to yellow and wherein the color change is detected visually.

24. The device of claim 22 wherein the dye changes color from red or purple to yellow and wherein the color change is detected by an instrument.

25. The device of claim 22 wherein the culture medium further comprises triphenyltetrazolium chloride.

26. The device of claim 25 wherein the triphenyltetrazolium chloride changes color in the presence of Enterobactericeae after about 24 hours.

* * * * *

UNITED STATES PATENT AND TRADEMARK OFFICE
CERTIFICATE OF CORRECTION

PATENT NO.: 5,723,308

DATED: March 3, 1998

INVENTOR(S): Patrick A. Mach, Karen E. Hesselroth, Carl A. Adams, Debra L. Schwab It is certified that error appears in the above-identified patent and that said Letters Patent is hereby corrected as shown below:

Col. 8, Table 1, Row S. saintpaul 373s under column RCCM - broth, under Acid/Gas, "(-/-)" should read --(+/-)--

Col. 15, line 6  "a dye" should read --a sulfonphthalein dye--

Signed and Sealed this

Fifteenth Day of May, 2001

Attest:

NICHOLAS P. GODICI

Attesting Officer

Acting Director of the United States Patent and Trademark Office